United States Patent [19]

Moore

[11] Patent Number: 4,472,353

[45] Date of Patent: Sep. 18, 1984

[54] GAS DETECTOR BADGE

[76] Inventor: Gerald Moore, 2310 Thayer, Evanston, Ill. 60201

[21] Appl. No.: 430,792

[22] Filed: Sep. 30, 1982

Related U.S. Application Data

[63] Continuation of Ser. No. 176,119, Aug. 7, 1980, abandoned.

[51] Int. Cl.³ .................... G01N 21/01; G01N 1/48
[52] U.S. Cl. ........................ 422/58; 422/56; 422/86; 422/87; 436/178
[58] Field of Search .............. 422/58, 56, 55, 87, 422/86, 83; 116/206; 73/23; 436/178

[56] References Cited

U.S. PATENT DOCUMENTS

| | | | |
|---|---|---|---|
| 2,249,867 | 7/1941 | Snelling | 73/335 |
| 2,606,102 | 8/1952 | Cook | 23/254 |
| 2,738,257 | 3/1956 | Darby | 23/232 |
| 2,823,984 | 2/1958 | Mavrodineanu | 23/232 |
| 3,480,402 | 11/1969 | Jackson | 116/206 X |
| 3,482,944 | 12/1969 | Plantz et al. | 422/87 |
| 3,723,064 | 3/1973 | Liotta | 422/56 X |
| 3,785,930 | 1/1974 | Ellis | 422/56 X |
| 3,809,617 | 5/1974 | Schmitt | 422/56 X |
| 3,884,641 | 5/1975 | Kraffczyk et al. | 23/253 R |
| 3,950,980 | 4/1976 | Braun et al. | 73/23 |
| 4,063,452 | 12/1977 | Bradshaw | 73/73 |
| 4,205,043 | 5/1980 | Esch et al. | 116/206 X |
| 4,225,557 | 9/1980 | Hartl et al. | 422/56 |
| 4,271,121 | 6/1981 | Diller et al. | 422/58 X |

Primary Examiner—Kenneth M. Schor
Attorney, Agent, or Firm—McDougall, Hersh & Scott

[57] ABSTRACT

A gas detector badge for detecting harmful gases, including a gas sensitive tape positioned behind a front panel, having an indicator window, a reference window and a control window. The control window is provided with a gas filter, whereas the indicator window is open to the atmosphere to permit harmful gas to pass through the indicator window to the gas sensitive tape; the reference window includes a gas impermeable member to protect the tape from the atmosphere. Harmful gases contacting the badge pass through the indicator window and the control window, passing through the latter at a slower rate, to chemically react with the tape to develop color as a measure of the harmful gases in the atmosphere.

10 Claims, 19 Drawing Figures

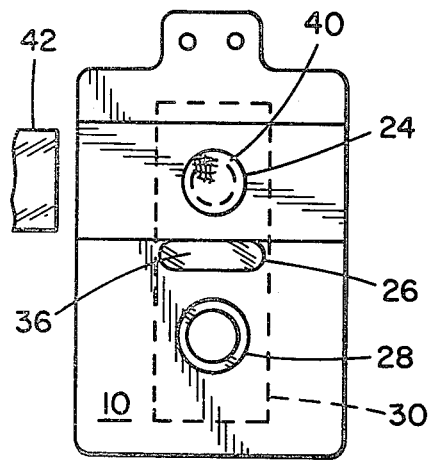
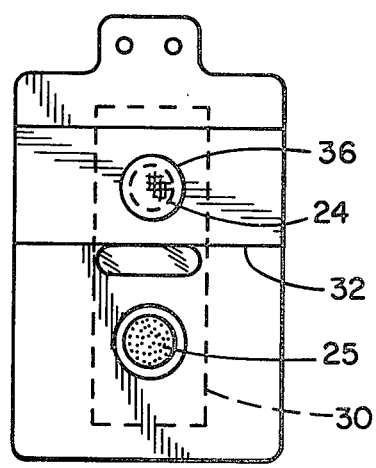
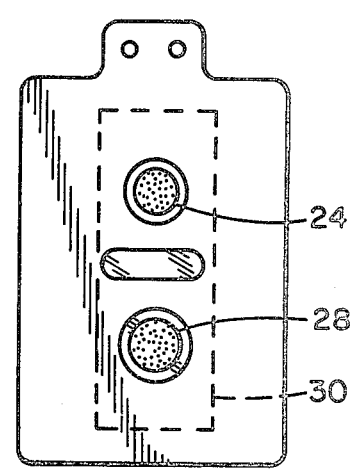
FIG.10  FIG.11  FIG.12
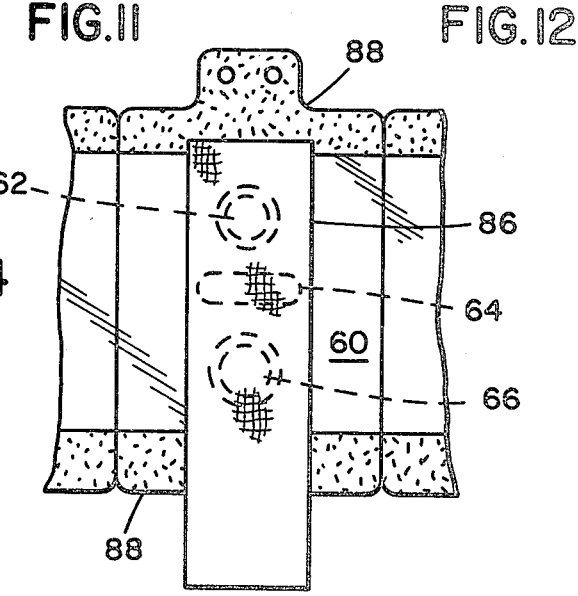
FIG.14
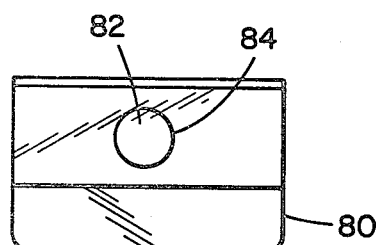
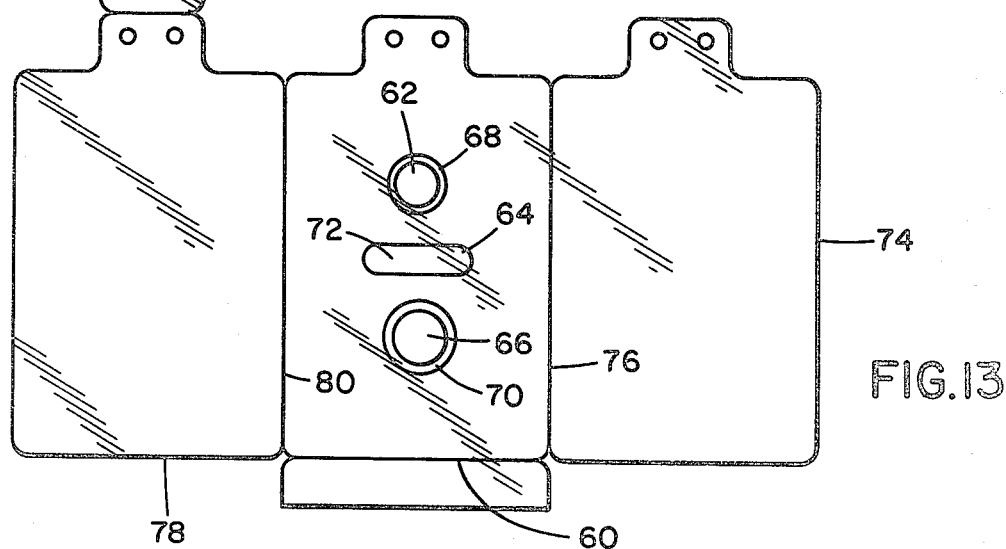
FIG.13

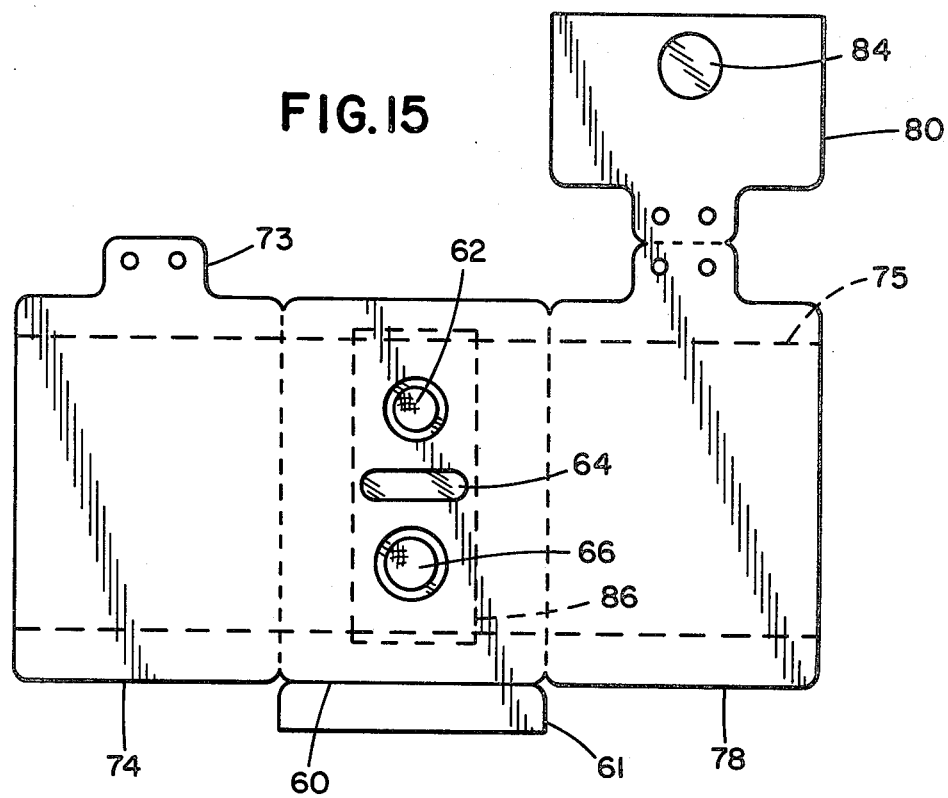
FIG.15
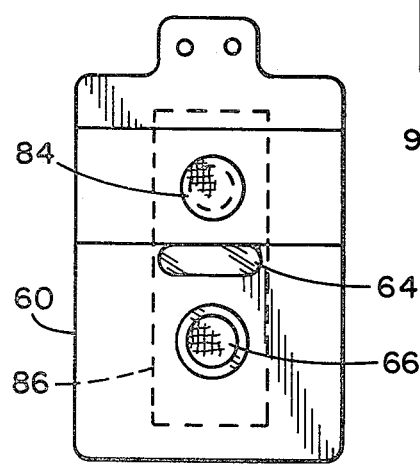
FIG.16
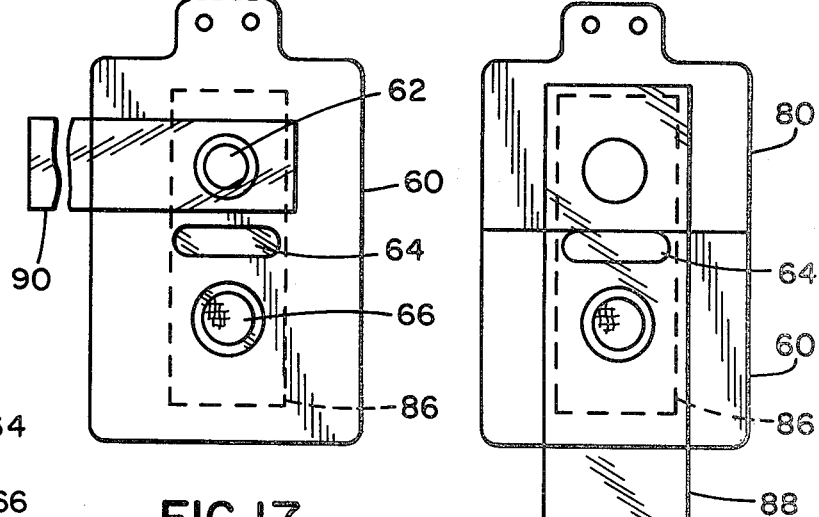
FIG.17
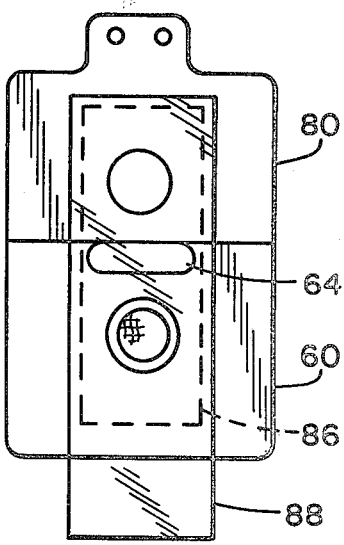
FIG.18
FIG.19

GAS DETECTOR BADGE

This application is a continuation of U.S. No. 176,119, filed Aug. 7, 1980 now abandoned.

This invention relates to a gas detector badge for detecting harmful gases, and more particularly to a disposable light-weight detector badge, preferably carried on the clothing of persons who potentially come into contact to such harmful gases.

A wide variety of dosimeters for detecting and measuring harmful gases have been proposed in the prior art. Typical of such devices is that shown in U.S. Pat. No. 3,482,944, describing a gas dosimeter employing a colorimetric strip which is also sensitive to light. The device shown in the foregoing patent includes a relatively complex housing for containing a replaceable paper strip which is chemically treated for reaction with various gases. However, the construction of that device, and particularly in the housing, does not lend itself to a relatively light-weight, disposable gas dosimeter.

In addition, the device as described in the foregoing patent cannot be conveniently adapted to have an extended range of gas concentrations or doses over which it is operable. A device of the latter type is shown in U.S. Pat. No. 3,950,980 in which the time-average amounts of harmful gases can be determined. However, devices of the sort described in the foregoing patent are complex in their construction, making them expensive and not readily adaptable for disposal after use.

It is accordingly an object of the present invention to provide a simple, disposable, light-weight gas detector badge for detecting harmful gases which overcomes the foregoing disadvantages.

It is a more specific object of the present invention to provide a gas detector assembly for detecting harmful gases in which the dose rate to which the individual wearing the badge has been exposed can be extended and determined simply and inexpensively.

These and other objects and advantages of the invention will appear more fully hereinafter, and, for purposes of illustration, but not of limitation, embodiments of the present invention are shown in the accompanying drawings wherein:

FIG. 10 illustrates, in plan view, a front panel just after it has been activated;

FIG. 11 illustrates the same view as FIG. 10 after exposure to harmful gases, with the filter in position;

FIG. 12 illustrates the same view as FIG. 11 after the filter has been removed to expose the underlying control window;

FIG. 13 illustrates, in plan view, an alternate form of the gas detector badge of this invention;

FIG. 14 illustrates the front panel of the device of FIG. 13 with the gas-sensitive strip in position;

FIG. 15 illustrates, in plan view, the view of FIG. 13 as viewed from the front panel;

FIG. 16 illustrates the assembly of the embodiment shown in FIGS. 13 and 15;

FIG. 17 illustrates the device of FIGS. 13 and 15 before the filter is moved into position;

FIG. 18 illustrates the view of FIG. 17 with the filter in position; and,

FIG. 19 illustrates the assembled form of the device of FIGS. 13-18.

The concepts of the present invention reside in a gas detector assembly for detecting harmful gases which includes a front panel defining three windows, an indicator window, a reference window and a control window. Underlying the windows of the front panel is at least one gas-sensitive layer adapted to develop color in response to contact with harmful gases. The gas-sensitive layer underlying the reference window is protected from the atmosphere by a gas impermeable layer or coating, preferably transparent, to prevent contact between the gas-sensitive layer underlying the reference window and harmful gases present in the atmosphere.

The gas-sensitive layer underlying the control window is protected by a filter. The filter serves three functions. In the first place, it acts as a diffusion barrier to extend the sensitivity range of the badge to higher doses of harmful gases. Secondly, it filters out potentially interfering materials, and particularly interfering gases. And, thirdly, it shields the gas-sensitive layer underlying the control window from potentially adverse effects caused by exposure to light.

Thus, in use, harmful gases in the atmosphere diffuse into contact with the gas-sensitive layer underlying both the indicator window and the control window to chemically react therewith and develop a color. The intensity of the color, relative to the color of the gas-sensitive layer underlying the reference window, is a measure of the amount of harmful gases present in the atmosphere. By utilizing an unprotected or open indicator window and a control window equipped with a filter, the range of doses measured by the badge of the invention can be extended. In addition, the use of a filter serves as a light shield for the gas-sensitive layer underlying the indicator window to insure that readings from the badge are not distorted by the effects of light.

The badge of the invention can thus be produced in a simple and economical manner, and readily lends itself to a disposable construction. It has been found that the badge of the invention provides accurate results which can be read quickly and inexpensively, without the need to employ complex auxiliary equipment.

Figure 1:
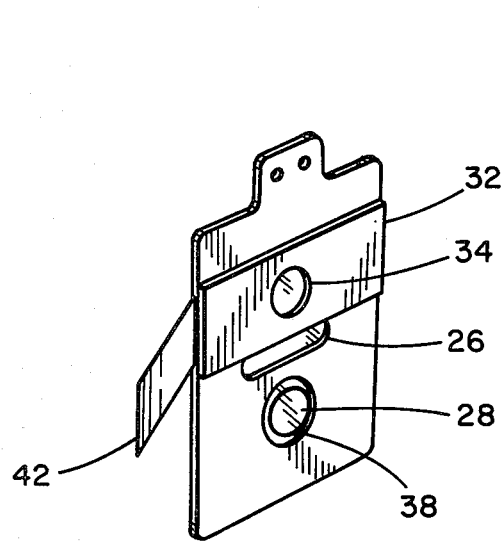
FIG. 1 is a view in perspective of one embodiment of the gas detector badge embodying the features of the present invention.
Figure 2:
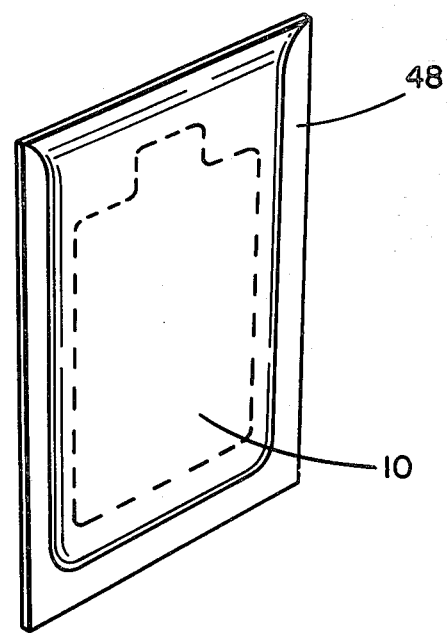
FIG. 2 is a view in perspective of one form of a sealed package for the badge shown in FIG. 1.
Figure 3:
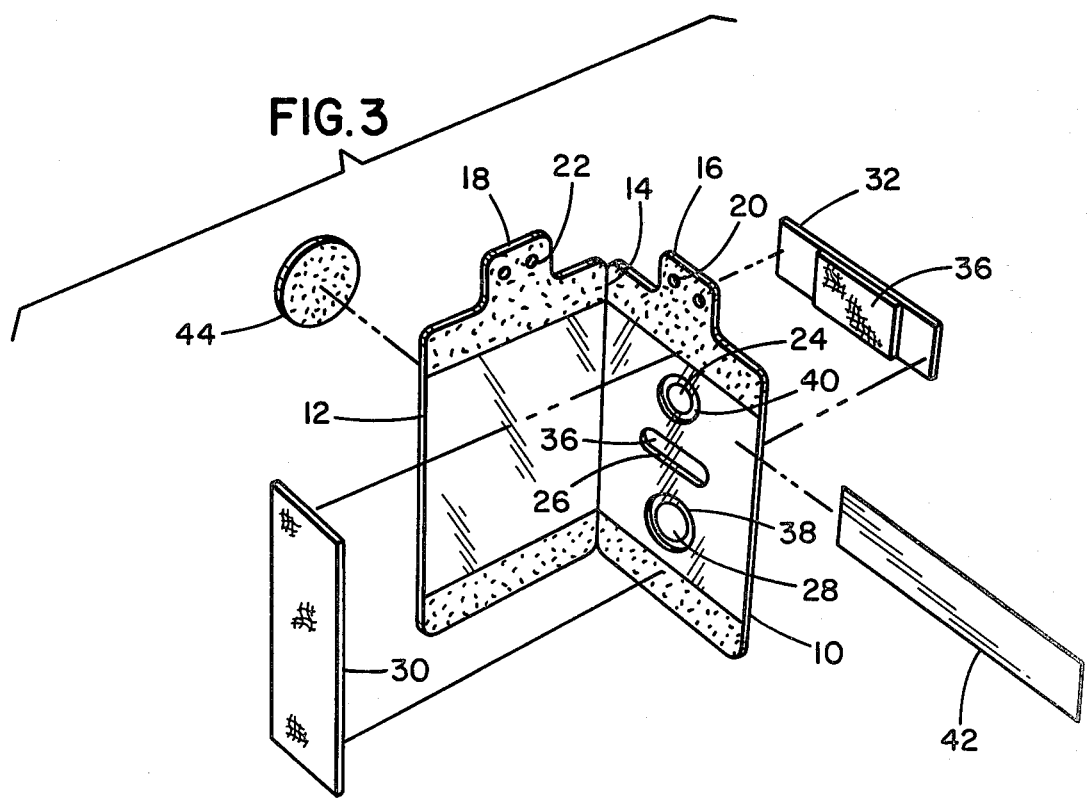
FIG. 3 is an exploded view in perspective illustrating the construction of the gas detector badge shown in FIG. 1.
Figure 4:
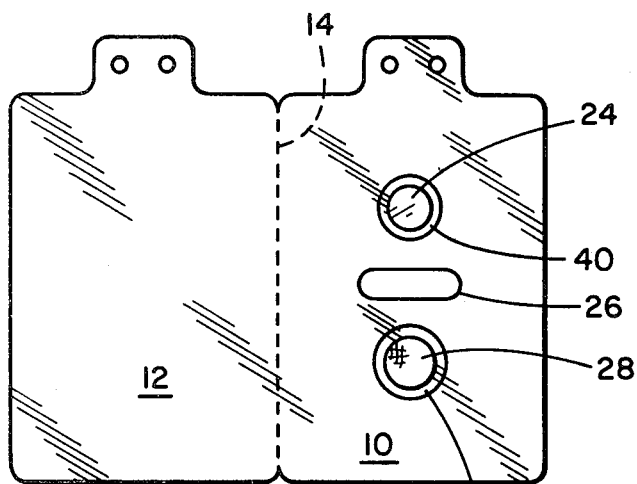
FIG. 4 is a plan view of the front and back panels of the device shown in FIGS. 1 and 3.
Figure 7:
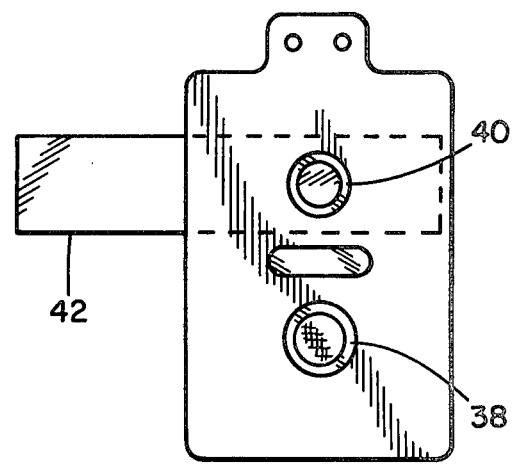
FIG. 7 illustrates a plan view of the front panel of the device shown in FIG. 6.
Figure 5:
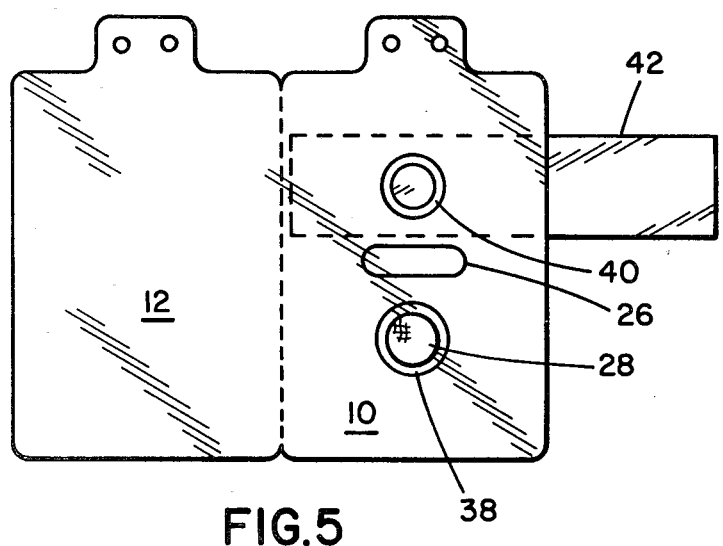
FIG. 5 is a plan view of the front and back panels of the badge shown in FIG. 1 including a removable, protective strip.
Figure 8:
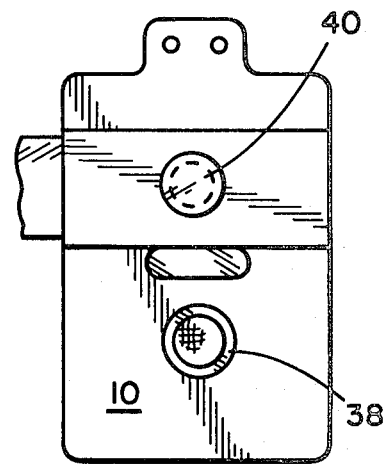
FIG. 8 illustrates, in plan view, a device as shown in FIG. 7 with a filter in position.

Referring now to the drawings for a more detailed description of the invention, there is shown in FIGS. 1 and 3 to 9 a badge embodying the features of the present invention. The device there shown includes a front panel 10, which can conveniently be made of paper, cardboard or like inexpensive materials when it is desired to have the badge of the invention in disposable form. Integral with the front panel 10 is a rear panel 12, and the two panels share a common edge 14 at which panel 10 can be folded over rear panel 12. As shown in FIGS. 1 and 3, both panels 10 and 12 can include a tab 16 and 18 equipped with one or more holes 20 and 22, serving to enable the badge to be attached to an article of personal clothing of the wearer.

The front panel includes a series of three openings, a control window 24, a reference window 26 and an indicator window 28. As shown in these figures, the control window 24 and the indicator window 28 are circular in configuration, although this particular shape is not important to the practice of the invention. Similarly, the reference window 26 is illustrated as an elongated slot 36, although its configuration is likewise unimportant to the present invention.

The badge also includes at least one gas-sensitive layer or tape 30 which is adapted to be positioned underlying the windows 24, 26 and 28. In the preferred form of the invention, the tape 30 is positioned against the three windows and then is secured into position by folding the rear panel 12 against the front panel 10 to sandwich the paper therebetween.

In its preferred form, the tape 30 is generally a paper tape which has been chemically impregnated with reagents capable of reaction with harmful gases in the atmosphere to produce a color, the intensity of which is proportional to the quantity of the harmful gases in the atmosphere. As will be appreciated by those skilled in the art, the type and amount of chemical reagents present in the tape 30 depends on the use to which the badge is put. Various reagents suitable for use in the practice of this invention are known in the literature. For example, the detection and measurement of phosgene can be detected by the classical Noweir and Pfitzer method as recommended by the American Industrial Hygiene Association in their analytical guide on phosgene promulgated in 1969. That system employs a combination of 4,4'-nitrobenzylpyridine and N-benzylaniline. However, as will be appreciated by those skilled in the art, numerous other reagents known to react with other gases to develop a color can be used instead.

In the embodiment shown in FIGS. 1-9, the filter employed to protect the gas-sensitive tape underlying the control window is a separate element adapted to be fixed over the control window. As is perhaps most clearly shown in FIGS. 1 and 3 of the drawing, an adhesive strip 32 having an opening 34 therein corresponds in dimension to the dimension of the control window 24. fixed to the adhesive strip 32 is a filter element 36 as shown in FIG. 3, and thus any gases passing through the opening 34 of the adhesive strip 32 must pass through the filter element 36 before passing through the control window 24. A particular filter element employed depends, in large measure, on the atmosphere in which the badge is to be used. In general, the filter element should serve to reduce the rate of diffusion of gases through the filter element itself so that the sensitivity of the badge of the invention can be extended. In addition, when employing the badge of this invention in atmospheres containing phosgene, the filter preferably serves to filter out hydrogen chloride gas, a frequent contaminant of phosgene. It has been found that hydrogen chloride gas can inhibit color formation and, in some circumstances, drastically reduce the color observed as a result of the reaction between phosgene and the chemical reagents on the chemical strip. Filters which remove doses of hydrogen chloride gas ranging up to 1200 parts per million-minutes are particularly suitable. Such filters are conventional and form no part of the present invention. In addition, the filter should be relatively translucent so as to shield the underlying gas-sensitive tape from the fading effects of light, particularly where the gas-sensitive tape is a tape sensitive to phosgene gas as described above.

In the preferred practice of the invention, the gas-sensitive tape 30 underlying the reference window 26 is protected against any harmful gases present in the atmosphere so that the color of the gas-sensitive tape may be used as a reference point after development of the color of areas of the tape underlying the control window 24 and/or the indicator window 28. For this purpose, the reference window 26 is provided with a gas-impermeable, but transparent barrier or film 36 as is perhaps best illustrated in FIG. 3 of the drawing. In that way, the area of the tape underlying the reference window 26 is clearly visible but retains its original color even though the badge may be contacted with an environment containing harmful gases.

In a preferred form of the invention, the indicator window is provided with a gas-impermeable member 38 which serves to protect a portion of the tape underlying the indicator window. As shown in FIGS. 1, 3 and 4-8, the partial gas barrier 38 is in the form of an annular ring concentric with the opening forming the indicator window 28, and is made of a gas-impermeable transparent member. The function of the barrier ring 38 is to provide direct contrast for observing color between the area in the center of the indicator window 28 after the harmful gases have reacted with the tape underlying the indicator window 28 and the tape underlying the barrier ring 38 which is protected against reaction. It has been found that the close proximity of the reacted and unreacted areas of the tape underlying window 28 does enable one to detect more readily a smaller difference in color intensity.

As shown in the drawings, the control window 24 may be equipped with a like barrier ring 40 serving the same purpose, but it is not necessary as readout of the badge is not normally effected by the wearer.

In accordance with another embodiment of the invention, there is provided a removable protective strip interposed between the front panel 10 and the gas-reactive tape 30 to prevent migration of components contained in the material forming the panel 10 to the gas reactive tape 30 which would tend to react with the tape 30 to form color therein. As shown in the drawings, the removable strip can be simply interposed between the tape 30 and the front panel 10 to cover the control window 24, and can simply be removed by pulling it from engagement between those two members, thereby providing communication between the control window 24 and the gas-sensitive strip or tape 30. Thus, the removable strip 42 is simply sandwiched between the tape 30 and the front panel 10 and is secured into position when rear panel 12 is folded over the gas-sensitive tape 30.

It is possible, and sometimes desirable, to provide the indicator window 28 with a like strip. The only important characteristics of this strip is that it be formed of a impermeable material to prevent the migration of reactants from the panels to the gas-sensitive tape 30.

The impermeable material also serves the important function of preventing migration of chemicals from the gas-sensitive tape 30 onto the filter element 36.

Figure 6:
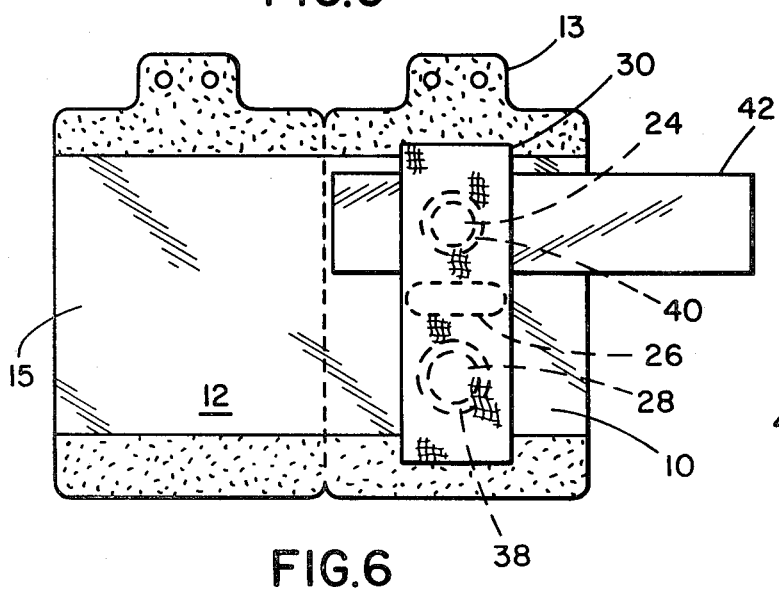
FIG. 6 illustrates the badge of FIG. 5 also including the gas-sensitive paper strip and inert plastic liner.

In accordance with the most preferred concept of the invention, the front and rear panels 10 and 12, respectively, are provided with an adhesive layer 13 substantially over the entire surface. Laid down over the adhesive layer 13 is a sheet of impermeable material 15, such as Tedlar, which is a trademark for polyvinyl fluoride. The adhesive portion 13 serves to secure the tape 30 in position since the tape 30 extends a short distance beyond the impermeable layer 15 to contact the adhesive layer 13 at its upper and lower ends. That type of construction represents a distinct advantage in terms of the manufacture of badges embodying the features of this invention on a mass scale. Thus, a card panel having the configuration of the front and rear panels 10 and 12 when laid out flat is simply provided with an adhesive coating, and then the strip 15 of impermeable material laid down over the adhesive 13 to secure the impermeable material 15 in position as shown in FIG. 6. Next, the removable protective strip 42 is laid in position followed by laying in position the gas reactive tape 30 such that it is secured to the adhesive layer 13 along its top and bottom edges as shown in FIG. 6. The last step of assembly thus involves folding rear panel 12 over onto the rear face of front panel 10 to sandwich therebetween the removable protective strip 42 and the tape 30. The corresponding areas 13 formed of the adhesive layer thus serve to secure front and rear panels 10 and 12, respectively, together to retain the structural integrity of the badge.

Figure 9:
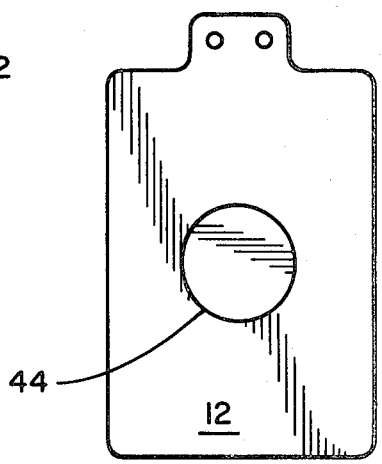
FIG. 9 is a plan view of the rear panel of the device shown in FIGS. 1 and 3-8.

As was indicated above, the badge can be secured to the clothing of the wearer by means of tabs 16 and 18. Alternatively, use can be made of an adhesive member 44 fixed to the rearward side of the rear panel 12 as shown in FIGS. 3 and 9. The adhesive disk 44 is secured to the rear panel 12, and can have a tear-away layer which, on removal, presents an adhesive surface so that the badge can simply be removably bonded to the clothing of the wearer.

It is frequently desirable to package the badge of the invention in a hermitically-sealed package to maximize its storage life. Use can be made of any conventional-type sealed package of the sort shown in FIG. 2 of the drawing where the badge 10 simply fits into an envelope 48 and is hermitically sealed therein.

Referring now to FIGS. 10-12 of the drawings, the badge of the invention is first activated by removal of the protective strip 42, thereby providing communication between the control window 24 and the gas-sensitive tape 30. Any hazardous gases present in the environment immediately react with the reagents contained in the gas-sensitive tape 30 to develop color therein. Since the area of the gas-sensitive tape underlying the indicator window 28 is totally unobstructed, that window and the underlying tape are capable, when detecting phosgene, of registering doses as low as 1 parts per million-minute, ranging up to color densities equivalent to doses of 100 parts per million-minute. beyond that dose level, the area of the tape 30 underlying the indicator window 28 becomes saturated.

However, the hazardous gas present in the atmosphere passes through the filter element 36 at a much lower rate, and hence the color development in the gas-sensitive tape underlying the control window 24 is significantly reduced. That has the effect of increasing the sensitivity or range of the badge up to dose levels of about 250 parts per million of phosgene in a phosgene system. As can be seen in FIG. 11, color develops immediately in the area of the tape 30 corresponding to the indicator window 28, while any color developed in the control window 24 is not visible due to the presence of the filter element 36. In processing, however, the removable layer 32 carrying the filter 36 is stripped away, thus exposing the area of the tape underlying the control window 24, which has undergone reaction with the hazardous gases present in the atmosphere. Due to the fact that the filter 36 serves as a diffusion barrier to slow down the rate of diffusion of harmful gases through the filter element 36, the color developed in the tape 30 in the area underlying the control window 24 is of lesser color intensity as compared to the area of the tape 30 underlying the indicator window.

To measure the dose received by the badge of the invention, the removable strip 32 carrying the filter is stripped away to expose the area of the tape 30 underlying the control window, and then the color intensity of the area of the tape 30 underlying the indicator window 38 and the area of the tape 30 underlying the control window 24 are compared to the color of the tape underlying the reference window 36. That comparison can be carried out by any of a number of methods well known to those skilled in the art. For example, it is possible to employ a color comparator having color wheels calibrated to various dose levels of, for example, phosgene. Thus, the area of the tape 30 underlying the control window 24 and the area of the tape underlying the indicator window 28 can simply be matched against the calibrated colors of the color comparator, and determined the phosgene dose to which the batch of this invention has been subjected.

Alternatively, use can also be made of a dosimeter reader employing an electronic electrical system to more accurately read color comparisons relative to the standard, the color of the tape 30 underlying the reference window 26. One such dosimeter which is particularly well suitable for use in the practice of this invention is a triple beam colorimeter designed to measure color by reflectance off the surface of the tape of the three windows. The color intensity of the area of the tape 30 underlying the indicator window 28 and the control window 24 relative to the area of the tape underlying the reference window 26 can then be correlated with, for example, phosgene doses.

Another embodiment of the present invention is illustrated in FIGS. 13 to 18. This embodiment includes a front panel 60 having a control window 62, a reference window 64 and an indicator window 66, with the control window 62 and the indicator window 66 again being provided with an annular barrier rings 68 and 70, respectively, serving the purposes described above. The reference window, as above, also includes a transparent barrier 72 which is a gas impermeable member.

Integral with the front panel 60 is a back panel 74, and the two panels share a common edge 76.

This embodiment also includes a middle panel 78 which is integral with the front panel 60 and shares a common edge 80 with it. Integral with the middle panel 78 is a foldable panel 80 carrying an opening 82 over which there is mounted a filter element 84.

As is best shown in FIGS. 14 and 15, the front panel 60 is provided with a layer of a gas-sensitive tape 86, which is of the same type as the strip 30 described above. The strip 86 is positioned in such a way as a portion of the underlying edge of the three windows of the front panel 60.

As was the case with the preceding embodiment, this embodiment too can be adapted for mass production by including an adhesive layer 73 overlying the entire surface of the front, middle and rear panels 60, 78 and 74, with the adhesive layer 73 being overlaid by a continuous strip of Tedlar 75 to insure that the tape 86 will be maintained in an inert environment. As before, both the top and bottom edges of the tape can be secured to the rear face of the front panel 60 by overlapping the tape 86 onto the adhesive layer 73.

To assemble the badge of this embodiment, the middle panel 78 is folded over, as shown in FIG. 17, to sandwich between the front panel 60 and itself the tape 86, and then the rear panel 74 is folded to underlie the middle panel 78.

Then, the tape 86 carrying the filter element is folded over so that the filter 84 covers the control window 62 to filter any gases diffusing through window 62 to the tape 86.

As before, the control window is also provided with a removable barrier or protecting layer 90 interposed between the front panel 60 and the foldable panel 80 to insure that the tape 86 is not inadvertently exposed to any hazardous gases prior to the time that monitoring of hazardous gases is desired.

In accordance with a variation on this concept, as shown in FIGS. 15 and 18, the removable barrier strip 88 is positioned so that, as shown in FIG. 18, it is interposed between the front panel 60 and the tape 86 as to all three windows. To insure that the adhesive 73 does not interfere with the removable barrier strip 88, the front panel is provided with a foldable tape 61 which is folded against the rear face of the front panel 60 to completely cover the adhesive 73 in that area. In that event, the adhesive 73 does not prevent removal of the barrier strip 88 since the area of the adhesive on the rear face of the front panel 60 is completely covered by the foldable panel 61.

As will be appreciated by those skilled in the art, the use of a Tedlar or other impermeable liner as described above is optional, depending somewhat on the materials of construction used and the type of gas sensitivity desired. Where the Tedlar strip is used, it has been found, in the manufacture of the badges of the present invention, that the Tedlar strip 75 as shown in FIG. 15 is advantageously laid down as a continuous strip over all three of the panels there shown. In the area of the reference window 64, the Tedlar liner is left intact, and thus the Tedlar lines serves as the impermeable barrier over the reference window 64. As to the indicator window 66, the Tedlar layer is provided with a punched opening, preferably a circular hole having a diameter less than the diameter of the indicator window. The annular portion of the Tedlar layer overlaying the indicator window thus serves as the partial barrier to provide the desired color contrast in the indicator window when reading the badge of the invention.

It will be understood that various changes and modifications can be made in the details of construction, procedure and use without departing from the spirit of the invention, especially as defined in the following claims.

I claim:

1. A gas detection assembly comprising:
   (a) a front panel having therein an indicator window, a reference window and a control window;
   (b) a gas sensitive layer underlying said windows, wherein said layer is adapted to develop color in response to contact with a harmful gas in the atmosphere as a measure of the amount of said gas contacting said layer;
   (c) a transparent gas impermeable layer positioned between the atmosphere and the portion of the gas sensitive layer underlying said reference window, thereby protecting the portion of the gas sensitive layer underlying said reference window from contact with that atmosphere; and
   (d) a filter positioned between the portion of said gas sensitive layer underlying said control window and the atmosphere, said filter slowing the rate of diffusion of the atmosphere to the portion of the gas sensitive layer underlying said control window relative to the rate of diffusion of the atmosphere to the portion of the gas sensitive layer underlying said indicator window, thereby causing the portion of the gas sensitive layer underlying said control window to indicate the presence of significantly higher doses of harmful gas in the atmosphere than that which is indicated by the portion of the gas sensitive layer underlying said indicator window.

2. An assembly as defined in claim 1 wherein said gas-sensitive layer means is a tape impregnated with chemicals capable of the development of color on reaction with said harmful gases, said tape being in the form of an elongate strip underlying each of said windows.

3. An assembly as defined in claim 1 which includes a back panel secured to said front panel to sandwich said gas-sensitive layer means therebetween.

4. An assembly as defined in claim 1 which includes a removable, gas-impermeable barrier positioned between the front panel and said gas sensitive layer to prevent passage of harmful gases to said gas-sensitive layer means.

5. An assembly as defined in claim 3 wherein the back panel is integral with said front panel whereby said back panel can be folded against the front panel.

6. An assembly as defined in claim 1 wherein at least one of the indicator window and the control window is partially covered with a transparent, gas impermeable layer to provide direct contrast between the color of said gas-sensitive layer means in contact with the atmosphere and the color of said layer means underlying said transparent, gas-impermeable layer.

7. An assembly as defined in claim 1 which includes a removable, gas-impermeable barrier positioned to prevent passage of any harmful gases through the control window to said gas-sensitive layer means.

8. An assembly as defined in claim 3 which includes a middle panel for folding against the front panel to secure said layer means therebetween.

9. An assembly as defined in claim 1 which includes a foldable panel for folding over the front panel, said foldable panel including an opening therein and said filter means positioned adjacent said opening whereby the filter means is positioned to filter gases passing through said control window when the foldable panel is folded over said front panel.

10. An assembly as defined in claim 1 wherein said gas-sensitive layer means is a paper tape impregnated with reagents capable of the development of color on contact with phosgene.

* * * * *